(12) United States Patent
Döring

(10) Patent No.: US 6,586,729 B2
(45) Date of Patent: Jul. 1, 2003

(54) ION MOBILITY SPECTROMETER WITH NON-RADIOACTIVE ION SOURCE

(75) Inventor: Hans-Rüdiger Döring, Leipzig (DE)

(73) Assignee: Bruker Saxonia Analytik GmbH, Leipzig (DE)

(*) Notice: Subject to any disclaimer, the term of this patent is extended or adjusted under 35 U.S.C. 154(b) by 0 days.

(21) Appl. No.: 10/132,065

(22) Filed: Apr. 25, 2002

(65) Prior Publication Data
US 2002/0185593 A1 Dec. 12, 2002

(30) Foreign Application Priority Data
Apr. 26, 2001 (DE) .......................... 101 20 336

(51) Int. Cl.⁷ .......................... H01J 49/00; H01J 49/40; B01D 59/44
(52) U.S. Cl. ................... 250/287; 250/281; 250/282; 250/286; 250/423 R; 250/423 P; 250/424; 250/435
(58) Field of Search ................ 250/287, 286, 250/281, 282, 423 R, 423 P, 424, 435

(56) References Cited

U.S. PATENT DOCUMENTS

| | | | | |
|---|---|---|---|---|
| 3,617,740 A | * | 11/1971 | Skillicorn | 250/492.1 |
| 4,707,602 A | * | 11/1987 | Knorr | 250/282 |
| 4,713,833 A | * | 12/1987 | Turner et al. | 378/119 |
| 4,940,300 A | * | 7/1990 | Giorgi | 252/181.5 |
| 5,245,192 A | * | 9/1993 | Houseman | 250/287 |
| 5,254,856 A | * | 10/1993 | Matsui et al. | 250/310 |
| 5,684,300 A | * | 11/1997 | Taylor et al. | 250/286 |
| 5,751,107 A | * | 5/1998 | Komatsu | 313/496 |
| 5,856,616 A | * | 1/1999 | Maswadeh et al. | 422/89 |
| 5,969,349 A | * | 10/1999 | Budovich et al. | 250/286 |
| 6,008,496 A | * | 12/1999 | Winefordner et al. | 250/423 P |
| 6,104,136 A | * | 8/2000 | Abe et al. | 313/258 |
| 6,107,624 A | * | 8/2000 | Doring et al. | 250/286 |
| 6,114,694 A | * | 9/2000 | Ito | 250/289 |
| 6,124,592 A | * | 9/2000 | Spangler | 250/282 |
| 6,144,029 A | * | 11/2000 | Adler | 250/286 |
| 6,147,449 A | * | 11/2000 | Iwasaki et al. | 313/310 |
| 6,179,678 B1 | * | 1/2001 | Kishi et al. | 445/24 |
| 6,429,426 B1 | * | 8/2002 | Doring | 250/286 |
| 2002/0185593 A1 | * | 12/2002 | Doring | 250/287 |
| 2002/0185594 A1 | * | 12/2002 | Doring | 250/287 |

FOREIGN PATENT DOCUMENTS

| | | |
|---|---|---|
| DE | 199 33 650 C1 | 3/2001 |
| GB | 2 315 154 A | 1/1998 |
| GB | 2 315 155 A | 1/1998 |

* cited by examiner

*Primary Examiner*—John R. Lee
*Assistant Examiner*—Bernard Souw

(57) ABSTRACT

An ion mobility spectrometer (IMS) is provided that has a non-radioactive electron source in an evacuated chamber that is separated from the reaction chamber of the IMS by an x-ray window. Electrons from the source impinge upon an x-ray anode, causing the emission of x-ray radiation toward the window. A current controller is provided by which currents in the electron-source chamber are monitored and controlled using a microprocessor circuit. If a maximum permissible residual gas pressure is exceeded, the electron source is automatically shut down and a gettering process is activated.

18 Claims, 1 Drawing Sheet

ION MOBILITY SPECTROMETER WITH NON-RADIOACTIVE ION SOURCE

FIELD OF THE INVENTION

The invention relates generally to ion mobility spectrometry and, more specifically, to the non-radioactive electron source of an ion mobility spectrometer (IMS).

BACKGROUND OF THE INVENTION

In the prior art there exists an ion mobility spectrometer having an evacuated electron source chamber which contains a non-radioactive electron source. The electron source is connected to the negative pole of an accelerating voltage source, and an x-ray anode is connected to the positive pole of the accelerating voltage source. X-ray radiation produced by electrons from the electron source impinging on the x-ray anode enters an adjoining reaction chamber of the IMS through a gas-tight x-ray window, which is impermeable to the electrons generated by the electron source. An IMS or method such as this is known from U.S. patent Ser. No. 09/617,716, which is incorporated by reference herein in its entirety.

The electron source of such an IMS must be operated in a vacuum. To ensure reliable and lasting operation, the pressure must be maintained at less than $10^{-3}$ mbar, and in some cases at less than $10^{-5}$ mbar. In such systems, the measurement process must be interrupted if the maximum permissible pressure is exceeded. However, because supply energy is very limited, it is undesirable to run a vacuum pump continuously. The volume of the electron source chamber is very small, and due to the presence of electrical vacuum feedthroughs, and the need for an x-ray window that is very thin, leakages into the chamber tend to occur. In addition, the risk of an unexpected additional micro-leak is always present.

SUMMARY OF THE INVENTION

In accordance with the present invention, an ion mobility spectrometer is provided that has a control electrode, in particular a Wehnelt cylinder, between the electron source and the anode of the electron source vacuum chamber. The anode current is regulated via the voltage on the control electrode, and an electrical circuit is provided that monitors the anode current between the positive and negative pole during operation. The invention also provides for a safety circuit to shut down the electron source in an emergency if a fault current between the anode and the control electrode exceeds a specified limit such as, for example, a current in the range from 1 nA to 1 $\mu$A.

The primary task of the control electrode, which has a more negative potential than the cathode during operation, is to control the intensity of the anode current. However, it can also be used to measure the undesirable ion current arising from the ionized background molecules. This serves as a measure of the residual gas pressure in the vacuum of the electron source chamber.

The electron source chamber may contain one or more getter pearls provided with electrical heat supplies. When thermally activated, one of these getter pearls will absorb the molecules of any residual gas coming into contact with it, thus improving the vacuum. In this way, each one of these pearls can, generally in a number of separate steps, improve the vacuum several times over. Altogether, each pearl can absorb several liters. In addition, a negative potential can be applied to the getter pearls so that the electrons are repelled and the positive residual gas ions are absorbed.

In one embodiment, the IMS contains an electron source in the form of a thermionic cathode, which can be electrically heated so that the anode current can be regulated via the heating power of the thermionic cathode. This can be used to shift the anode current within wide ranges. In particular, it can be significantly increased for short periods, if necessary, in order to increase the sensitivity of the measurement.

In an alternative embodiment, the electron source contains a cold emitter so that the anode current can be regulated via the potential of the control electrode. Unlike thermionic electrodes, the cold-emitter technology has the advantage that it consumes less energy and has a longer service life. In particular, the surface structure of the cold emitter still offers many possibilities for adaptation to the actual problem as well as optimization. The potential of the cold emitter, in relation to the control electrode, may lie between +5 V and +50 V. Within this range, the anode current can be adjusted very well by varying the potential of the control electrode.

Also provided by the present invention is the use of an electrical circuit that interrupts the operation of the IMS for a specified time period. Such a time period may be between 5 and 15 minutes. The circuit also switches on the getter heating system in the event of the fault current exceeding a threshold value, such as between 1 nA and 1 $\mu$A. If the system is switched off at a fault current of approximately 1 $\mu$A, the IMS may require several hours to reach its optimum operating state, after the subsequent gettering. During this time, the anode current may be increased by, for example, increasing the heating of the thermionic cathode in order to provide sufficient sensitivity. However, it is possible to perform the gettering even when the pressure is significantly lower than the maximum permissible pressure when the fault current is within the range from 1 to 10 nA. In such a case, the operation of the IMS does not have to be interrupted.

When the IMS is operating, it is advantageous to regulate the anode current to a set-point value, in particular, within the range of 1 to 500 $\mu$A, and to maintain this value via the control voltage or, if necessary, the heating system for the thermionic cathode. At the same time, the spectra will be produced at a constant sensitivity so that they can be easily compared with one other.

When starting up the IMS or restarting the IMS after the gettering or after maintenance work, the anode current should be slowly regulated to the set-point value within a period of 1 to 10 minutes while keeping to the maximum permissible fault current. This has the advantage that the instrument cannot unexpectedly get into an operating state which would damage the electron source.

With the thermionic cathode, a thermistor (in particular a TNA type) can be integrated into the heating current circuit so that the heating current can only increase slowly. This is due to the fact that the ohmic resistance of the thermistor is initially large and decreases slowly only when the thermistor heats up under constant current loading, so that the heating current continuously increases until it reaches the equilibrium value. Of course, the anode current can still be regulated via the heating power even in the presence of the thermistor. It limits the rate at which the heating current increases only via the hardware.

In an illustrative embodiment of the invention, the electron source chamber is made predominantly from metal, for example stainless steel. Although a housing made from glass might provide better performance in the areas of vacuum tightness and degassing, a metal housing is by far the simpler to manufacture, can be made with greater precision and is easier to fit to the x-ray window mounting and other components of the IMS. The above-mentioned measures can be fully exploited to improve and monitor the vacuum. Metallic materials, such as stainless steels, may be used that are optimized in regard to their degassing properties by total or surface pretreatment, using thermal, mechanical or chemical methods.

The x-ray window is preferably made from beryllium, possibly with a thickness between 10 $\mu$m and 100 $\mu$m and with an effective diameter between 3 mm and 20 mm. Beryllium is used as the window material because of its low atomic number. This metal has the required vacuum tightness and mechanical stability for the given thicknesses and diameters under a pressure difference of 1 bar.

In one embodiment, an arrangement of the components in the electron-source chamber and the x-ray window is such that no electrons emitted by the electron source reach the x-ray window. This is achieved, for example, by a configuration in which the electrons are accelerated approximately parallel to the partition, and arrive at the anode at an angle of 45°, generating x-ray radiation (characteristic radiation and/or bremsstrahlung) toward the window. Only the x-ray radiation hits the x-ray window, so that the window is not polluted with electrons.

The x-ray anode may also be applied to the x-ray window on the vacuum side as a thin coating, for example, less than 500 nm. In such a case, electrons arriving from the electron source are stopped in the metal coating and produce x-radiation which enters the x-ray window and penetrates it. In one embodiment, the metal coating is at least as thick as seven half-value thicknesses of the penetrating electrons that arrive from the electron source so that few, if any, electrons reach the x-ray window directly. Due to the conductivity of the metal coating, the thermal loading is also relatively low. It may also be desirable to keep the metal coating at a thickness of less than two half-value thicknesses of the x-rays produced. This ensures that the intensity of the x-radiation passing through the x-ray window into the reaction chamber is still sufficient.

The anode material may include all metals with a high atomic number such as tungsten and gold. In such a case, bremsstrahlung is predominantly used. However, light elements may also be used. Materials such as aluminum or magnesium produce characteristic radiation is in a very favorable range. This radiation is such that ionization of the air components in the reaction chamber, predominantly nitrogen and oxygen, takes place with a large activation cross-section via their K shells at energies of approx. 400 to 500 eV.

The acceleration voltage of the system may be kept below 5 kV. This is sufficient to produce x-ray radiation that is intense enough to penetrate the window and ionize a sample in the reaction chamber directly or via photoelectrons (as discussed in the aforementioned U.S. patent application Ser. No. 09/617,716). The range in air at atmospheric pressure is very suitable for the geometric dimensions of the reaction chamber. Furthermore, the appropriate voltages are still easy to handle without having to take extreme safety precautions. The x-ray window may also be stabilized mechanically by a support grid. The x-ray window can therefore be thinner and/or have a larger useful diameter.

It may also be desirable for the support grid to be predominantly on the side facing away from the vacuum. An arrangement such as this prevents the support grid from being impacted by electrons from the electron source, which would produce a considerable amount of useless bremsstrahlung. Furthermore, if the grid was on the electron source chamber side of the window, and the anode was attached to the x-ray window, the anode and the support grid would interfere with each other. Having the support grid on the other side of the window, on the other hand, may also be utilized to produce photoelectrons in the ionization chamber. The support grid may be metallically bonded to the x-ray window so that it can hold and stabilize the window against overpressure.

BRIEF DESCRIPTION OF THE DRAWINGS

An illustrative embodiment of the invention will now be described with reference to the accompanying drawing, in which.

DETAILED DESCRIPTION

Figure 1:
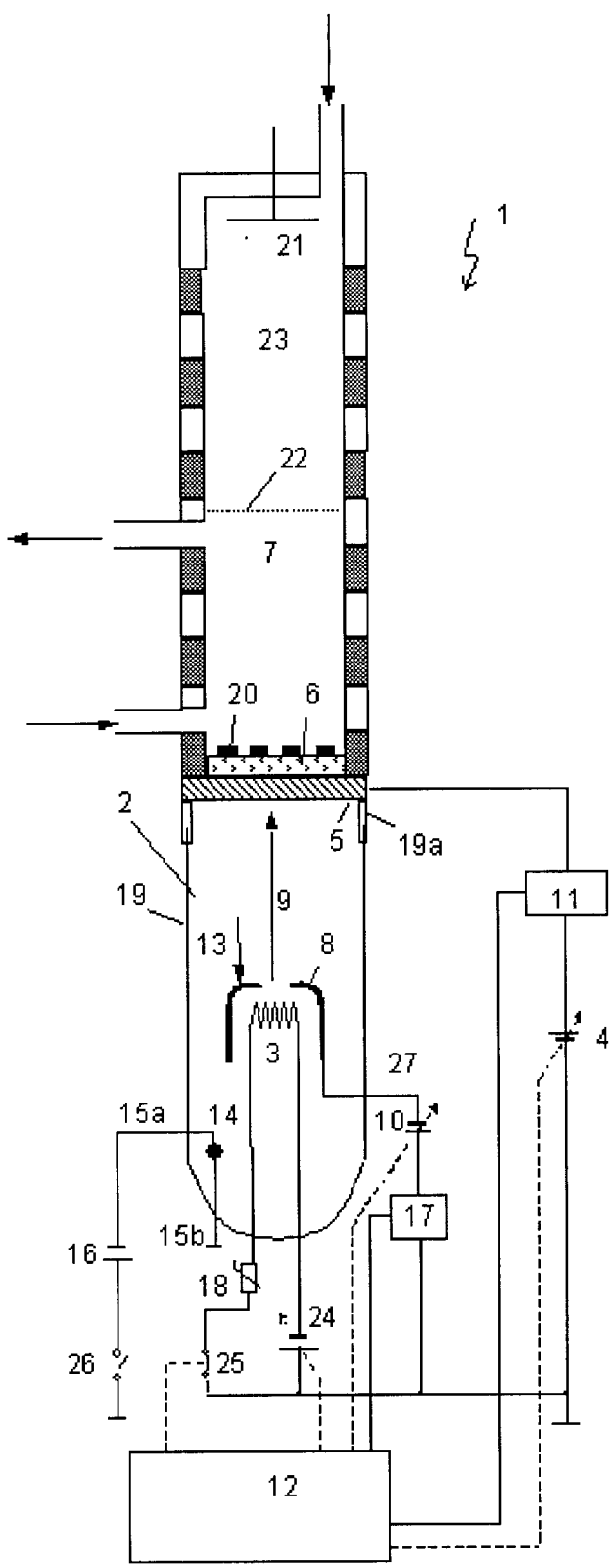
FIG. 1 shows a schematic structure of an IMS according to the invention.

In detail, FIG. 1 shows schematically the construction (not to scale) of an ion mobility spectrometer (IMS) 1 according to the invention. An IMS or method similar to this is known from U.S. patent Ser. No. 09/617,716, which is incorporated by reference herein in its entirety. The IMS of FIG. 1 has an evacuated electron-source chamber 2 and an adjacent reaction chamber 7 to which, after a switchable grid 22, a drift chamber 23 is connected, the end of which has an ion detector 21. The electron-source chamber 2 and reaction chamber 7 are separated by a vacuum-tight x-ray window 6 made from beryllium with a thickness of 25 $\mu$m and a free diameter of 5 mm. The x-ray window is metallized with a 100 nm thick aluminum coating 5 that serves as the anode. The window is retained on the reaction-chamber side by a honeycombed support grid made from nickel. The mesh of the honeycomb is 300 $\mu$m, the transparency is 80% and the thickness is 50 $\mu$m. The nickel grid 20 is applied onto the beryllium window 6 by electro-deposition and therefore bonded fast to it. The electron source chamber 2 has a stainless steel housing 19 that is electrically isolated from the anode 5 and the window mounting via an insulator ring 19a. The electron-source chamber contains a thermionic cathode 3 that serves as a non-radioactive source. The cathode 3 is connected to a variable, electronically-controllable heater voltage source 24 via insulated, vacuum-tight feedthroughs and a thermistor 18. Between the anode 5 and the heater voltage source 24 there is an accelerating voltage 4 of 1.8 kV during operation. A circuit 11 for monitoring the anode current 9 is integrated in the accelerating voltage circuit. Between the thermionic cathode 3 and the anode 5 there is a control electrode 8 in the form of a Wehnelt cylinder. A voltage source 10 is positioned between the control electrode 8 and the heater voltage source 24. The control electrode voltage is supplied via an insulated feedthrough 27 and can be controlled between −5V and −50 V. A fault current 13 flowing via the control electrode 8, which is produced, for example, by positive residual gas ions, is recorded by the circuit 17. In the electron-source chamber 2 there is also a getter pearl 14 which can be heated by means of a switchable voltage source 16 via the insulated feedthroughs 15a and 15b. A safety circuit 12 having a microprocessor controls the voltage sources 4, 10 and 24 depending on the size of signals in circuits 11 and 17. The heating currents for the thermionic cathode 3 and getter pearl 14 are switched on and off by the microprocessor circuit 12 via switches 25 and 26.

In an illustrative embodiment, the length of the electron source chamber 2 is 50 mm and its external diameter is 20 mm. When starting the IMS, the anode voltage 4 and the controller voltage 10 are applied first. After this, the thermionic cathode 3 is heated up under the control of the microprocessor circuit and the thermistor 18. As a result, an anode current 9 builds up which is recorded by the microprocessor circuit 12 via the monitor circuit 11. If there are appreciable amounts of residual gas in the evacuated electron source chamber 2, some will be converted into ions by the anode current 9. As such, a fault current 13 will be generated which will flow to the control electrode 8, be recorded by the circuit 17 and reported to the microprocessor circuit 12. If this fault current 13 exceeds a threshold value of 10 nA, then the switch 26 will close. This will activate the getter pearl 14 for a fixed period, e.g., 10 minutes. After this, the switch 26 will open again and the start-up will be continued. If, during operation, the fault current 13 should exceed the threshold value again, the microprocessor circuit 12 will activate the getter pearl heater again while the IMS measurement continues. If the fault current is between 0.1 and 1 $\mu$A, which may occur, for example, after the evacuated electron source chamber has been stored for a long time, the microprocessor will switch off the thermionic cathode heater via switch 25 and the getter process will take place with the thermionic cathode 3 switched off.

What is claimed is:

1. An ion mobility spectrometer comprising:
   an evacuated electron-source chamber;
   a reaction chamber separated from the electron source chamber by a gas-tight x-ray window that is substantially impermeable to electrons generated by the electron source;
   a non-radioactive electron source and an x-ray anode located within the chamber such that electrons from the electron source impinge upon the anode to cause x-ray radiation to be generated toward the window;
   a current controller including a control circuit and a control electrode that is located between the electron source and the anode, the controller regulating anode current by monitoring the anode current with the control circuit and controlling the voltage on the control electrode in response thereto; and
   a getter located in the electron-source chamber, activation of the getter being electrically controlled by the control circuit.

2. An ion mobility spectrometer according to claim 1 wherein the getter has an activating heater that may be electrically controlled.

3. An ion mobility spectrometer according to claim 2 wherein a negative potential is applied to the getter.

4. An ion mobility spectrometer according to claim 1 further comprising a safety circuit that determines whether a fault current between the anode and the control electrode has exceeded a predetermined limit and, if so, interrupts the operation of the IMS for a specified time period.

5. An ion mobility spectrometer according to claim 4 wherein the getter has an activating heater that may be electrically controlled, and wherein the heater is activated during said interruption of the IMS operation.

6. An ion mobility spectrometer according to claim 1 wherein the electron source comprises an electrically heated thermionic cathode, and wherein the anode current may be regulated via heating power of the thermionic cathode.

7. An ion mobility spectrometer according to claim 6 wherein a thermistor is integrated into the heating circuit of the thermionic cathode so as to limit the rate of increase of the heating current.

8. An ion mobility spectrometer according to claim 1 wherein the electron source comprises a cold emitter, and wherein the anode current may be regulated via the potential of the control electrode.

9. An ion mobility spectrometer according to claim 8 wherein a potential difference between the cold emitter and the control electrode is between +5V and an accelerating voltage of an accelerating voltage source to which the electron source is connected.

10. An ion mobility spectrometer according to claim 8 wherein a potential difference between the cold emitter and the control electrode is between +5V and 50 V.

11. An ion mobility spectrometer according to claim 8 wherein during operation, the anode current is regulated to a set-point value between 1 and 500 $\mu$A.

12. An ion mobility spectrometer according to claim 1 wherein the electron source chamber comprises a housing that is made predominantly from stainless steel.

13. An ion mobility spectrometer according to claim 1 wherein the x-ray window comprises beryllium.

14. An ion mobility spectrometer according to claim 13 wherein the x-ray window has a thickness of between 10 $\mu$m and 100 $\mu$m and an effective diameter of between 3 mm and 20 mm.

15. An ion mobility spectrometer according to claim 1 wherein the anode comprises a thin coating of less than 500 nm attached to a side of the x-ray window facing the reaction chamber.

16. An ion mobility spectrometer according to claim 1 wherein an accelerating voltage connected to the anode and the electron source is less than 5 kV.

17. An ion mobility spectrometer comprising:
   an evacuated electron-source chamber;
   a reaction chamber separated from the electron-source chamber by a gas-tight x-ray window that is substantially impermeable to electrons generated by the electron source;

a non-radioactive electron source located within the chamber which is connected to the negative pole of an accelerating voltage source;

an x-ray accelerating anode located within the chamber which is connected to the positive pole of the accelerating voltage source, the source and anode being such that electrons from the electron source impinge upon the anode and cause x-ray radiation to be emitted toward the window;

a current controller including a control circuit and a control electrode that is located between the electron source and the anode, the controller regulating anode current by monitoring the anode current with the control circuit and controlling the voltage on the control electoron in response thereto;

a monitoring circuit that monitors the anode current between the positive and negative pole during operation and a safety circuit that shuts down the electron source if a fault current between the anode and the control electrode exceeds a specified limit; and at least one getter pearl located in the electron-source chamber, the getter pearl having an activating heater that may be electrically controlled.

18. An ion mobility spectrometer according to claim 17 wherein, during operation, the anode current is regulated to a set-point value between 1 and 500 $\mu$A, wherein a housing of the electron source chamber is made predominantly from stainless steel, wherein the x-ray window comprises beryllium and has a thickness of between 10 $\mu$m and 100 $\mu$m and an effective diameter of between 3 mm and 20 mm and wherein a voltage of the accelerating voltage source is less than 5 kV.

* * * * *